United States Patent [19]
Tickner et al.

[11] Patent Number: 6,008,357
[45] Date of Patent: Dec. 28, 1999

[54] RESOLUTION OF 1-AZABICYCLO[2.2.2] OCTAN-3-AMINE, 2-(DIPHENYLMETHYL)-N-[[2-METHOXY-5-(1-METHYLETHYL) PHENYL]METHYL]

[75] Inventors: Derek L. Tickner, Waterford; Morgan Meltz, Niantic, both of Conn.

[73] Assignee: Pfizer Inc, New York, N.Y.

[21] Appl. No.: 08/981,750

[22] PCT Filed: Jul. 4, 1996

[86] PCT No.: PCT/IB96/00648

§ 371 Date: Dec. 16, 1997

§ 102(e) Date: Dec. 16, 1997

[87] PCT Pub. No.: WO97/03984

PCT Pub. Date: Feb. 6, 1997

Related U.S. Application Data

[60] Provisional application No. 60/001,191, Jul. 17, 1995.

[51] Int. Cl.$^6$ .................................................. C07D 453/02
[52] U.S. Cl. ............................................................. 546/133
[58] Field of Search ............................................... 546/133

[56] References Cited

U.S. PATENT DOCUMENTS

| | | | |
|---|---|---|---|
| 5,162,339 | 11/1992 | Lowe, III | 514/305 |
| 5,604,241 | 2/1997 | Ito et al. | 514/305 |
| 5,807,867 | 9/1998 | Ito et al. | 514/305 |

FOREIGN PATENT DOCUMENTS

| | | |
|---|---|---|
| 9104253 | 4/1991 | WIPO . |
| 9220676 | 11/1992 | WIPO . |
| 9221677 | 12/1992 | WIPO . |

OTHER PUBLICATIONS

Jacques et al., Enantiomers, Racemates, and Resolutions, pp. 380–383, 1981.

Bayley et al., "Resolution of Racemates by Diastereomeric Salt Formation", Chirality in Industry, pp. 70–77, 1992.

Eliel et al., Stereochemistry of Organic Compounds, pp. 322–381, 1994.

*Primary Examiner*—Mukund J. Shah
*Assistant Examiner*—Brenda Coleman
*Attorney, Agent, or Firm*—Peter C. Richardson; Paul H. Ginsburg; Jacob M. Levine

[57] ABSTRACT

A process for resolving 1-azabicyclo[2.2.2]octan-3-amine, (2-diphenylmethyl)-N-[[2-methoxy-5-(1-methylethyl) phenyl]methyl] in which 1-azabicyclo[2.2.2]octan-3-amine, (2-diphenylmethyl)-N-[[2-methoxy-5-(1-methylethyl) phenyl]methyl] is reacted with 1R-(-)-10-camphorsulfonic acid in a solvent capable of dissolving both the foregoing reactants and selectively dissolving the camphorsulfonic acid salt of the corresponding (2R, 3R) enantiomer relative to the (2S, 3S) enantiomer.

14 Claims, No Drawings

RESOLUTION OF 1-AZABICYCLO[2.2.2] OCTAN-3-AMINE, 2-(DIPHENYLMETHYL)-N-[[2-METHOXY-5-(1-METHYLETHYL) PHENYL]METHYL]

REFERENCE TO RELATED PROVISONAL AND INTERNATIONAL APPLICATIONS

This application is a 371 of PCT/IB96/00648, filed Jul. 4, 1996, which claims benefit of U.S. Provisional Application Ser. No. 60/001,191, filed Jul. 17, 1995.

This invention relates to a process for resolving 1-azabicyclo[2.2.2]octan-3-amine, 2-(diphenylmethyl)-N-[[2-methoxy-5-(1-methylethyl)phenyl]methyl].

The above compound (hereinafter also referred to as "the racemate") and the (2S, 3S) enantiomer of such compound (hereinafter also referred to as "the (2S, 3S) enantiomer") are substance P receptor antagonists that are useful in the treatment and prevention of a wide variety of central nervous system, gastrointestinal, inflammatory and other disorders. The racemate and the (2S, 3S) enantiomer, as well as methods by which they can be prepared, are referred to in U.S. patent application Ser. No. 08/211,120, which was filed on May 23, 1994 as the U.S. national phase of International Patent Application PCT/U.S. 92/03317, which was filed on Apr. 28, 1992. U.S. patent application Ser. No. 08/211,120 is incorporated herein by reference in its entirety. Both the above compounds and methods for preparing them are referred to, generically, in U.S. Pat. No. 5,162,339, which issued on Nov. 10, 1992. This patent is also incorporated herein by reference in its entirety.

SUMMARY OF THE INVENTION

This invention relates to a process for resolving 1-azabicyclo[2.2.2]octan-3-amine, 2-(diphenylmethyl)-N-[[2-methoxy-5-(1-methylethyl)phenyl]methyl] comprising reacting 1-azabicyclo[2.2.2]octan-3-amine, 2-(diphenylmethyl)-N-[[2-methoxy-5-(1-methylethyl) phenyl]methyl] with 1R-(-)-10-camphorsulfonic acid in an appropriate solvent to form the camphorsulfonic acid salt of (2S, 3S)-1-azabicyclo[2.2.2]octan-3-amine, 2-(diphenylmethyl)-N-[[2-methoxy-5-(1-methylethyl) phenyl]methyl], and then optionally hydrolyzing such salt to obtain the free base of the (2S, 3S) enantiomer.

The method of the present invention is a substantial improvement over the most practical of the methods described heretofore for preparing the (2S, 3S) stereoisomer of 1-azabicyclo-[2.2.2]octan-3-amine, 2-(diphenyl-methyl)-N-{[2-methoxy-5-(1-methylethyl)phenyl]methyl}, described in detail further below as the method beginning with a compound of formula XI, which has the same absolute stereochemistry as the desired product. This method is also described in detail in above-cited WO 92/21677. In this method a compound of formula XI is subjected to catalytic debenzylation whereby the benzyl or methoxy-benzyl group at the 3-position is hydrolytically removed to give the corresponding 3-amine, i.e., a compound of formula VI, with the same desired stereochemistry. Compound VI is then reacted with a compound of formula VII, which is an aldehyde comprising the desired group: 2-methoxy-5-(1-methylethyl)-phenylmethyl, to yield the desired final product having said desired group at the 3-position as well as the desired stereochemistry.

A compound of formula XI, the starting material for the above-described prior art method, is prepared by reductive amination of 3-keto-2-benzhydrylquinuclidine, in accordance with procedures such as the ones described in U.S. Pat. No. 5,162,339 under "Preparation F". These procedures comprise reductive amination of commercially available 3-keto-2-benzhydrylquinuclidine having the desired 2S configuration, using the primary amines benzylamine or methoxy-benzylamine, followed by reduction of the resulting imine intermediate to provide the amine of formula XI. Accordingly, the above-described preferred method of the prior art for preparing the (2S, 3S) or (2S, cis) enantiomer of 1-azabicyclo-[2.2.2]octan-3-amine, 2-(diphenyl-methyl)-N-{[2-methoxy-5-(1-methyl-ethyl)-phenyl]methyl}, may be described as initially comprising the following two steps: (1) subjecting 3-keto-2-benzhydrylquinuclidine having the desired 2S stereochemistry, to reductive amination with benzylamine or methoxybenzylamine to give the corresponding 3-(benzyl or methoxybenzyl)amine and separating out the desired 2S, 3S diastereomer of formula XI; followed by (2) catalytic debenzylation to give the corresponding 3-amine of formula VI having the desired stereochemistry, which is later reacted with an aldehyde of formula VII, as already mentioned.

The method of the present invention is an improvement over the above-described preferred method of the prior art because it unexpectedly permits elimination of the two above-recited steps while still providing a stereoselective preparation which provides the 2S,3S desired final product at very high purity levels. This surprising result is achieved by starting with 3-keto-2-benzhydrylquinuclidine as in the above-described prior art method, but then reacting it with [2-methoxy-5-(1-methylethyl)phenyl]methylamine. This reaction is a reversible nucleophilic addition reaction resulting in an unstable carbinolamine intermediate, which undergoes dehydration to give the corresponding imine. This dehydration is acid catalyzed using, e.g., 1R-(-)-10-camphorsulfonic acid with the addition of heat by refluxing and is driven to completion by the removal of water as it is formed.

An especially favorable aspect of this reaction is the action of the bulky benzhydryl group which by a steric mechanism results in the nearly exclusive formation of the cis diastereomer, i.e., the 2R,3R and 2S,3S enantiomers of the product of formula III. This leads directly to the resolution step of the method of the present invention in which the product of formula III is reacted with 1R-(-)-10-camphorsulfonic acid, not as an acid for catalyzing dehydration of a carbinolamine to form an imine, but in order to form the chiral salts of the 2R,3R and 2S,3S enantiomers of the product of formula III. The use of 1R-(-)-10-comphorsulfonic acid for the resolution of optically active isomers is already known. See, e.g., The Merck Index, 12th ed., 1996, Susan Budavari ed., Merck & Co., Inc., Whitehouse Station, N.J. However, it was unexpected that this method could be applied to separate the 2R,3R and 2S,3S enantiomers produced by the reactions depicted in Scheme 1 and further described herein, and that it would thereby be possible to eliminate two steps from the preferred prior art method of preparing the same final product, and gain the benefit of the resulting efficiencies.

Said enantiomers are separated in a facile manner by utilizing a solvent which will dissolve both of the reactants, i.e., the 1R-(-)-10-camphorsulfonic acid and the product of formula III, as well as the 2R,3R enantiomer. The desired (2S,3S) enantiomer of 1-azabicyclo-[2.2.2]octan-3-amine, 2-(diphenyl-methyl)-N-{[2-methoxy-5-(1-methylethyl)-phenyl]methyl} is thus readily removed by precipitation from the reaction solution as the 1R-(-)-10-comphorsulfonic acid salt, which can be hydrolyzed to give the free amine base.

The solvent for the resolution step of the present invention can be any solvent that is capable of resolving both the racemate and the camphorsulfonic acid resolving agent and of selectively dissolving the camphorsulfonic acid salt of the corresponding (2R,3R) enantiomer relative to that of the (2S,3S) enantiomer. Examples of such solvents are acetonitrile acetone and ethanol. Acetonitrile is preferred.

The camphorsulfonic acid salt of the (2S, 3S) enantiomer that is obtained from the above resolution process can be optionally repulped as exemplified in section B, paragraph 2 of the Example, to increase the optical purity of the product.

DETAILED DESCRIPTION OF THE INVENTION

Scheme 1 below illustrates a method by which the racemate can be prepared. Scheme 2 below illustrates the resolution of the racemate to form the camphorsulfonic acid salt of the (2S, 3S) enantiomer. Scheme 3 illustrates the cleavage of the camphorsulfonic acid salt of the (2S, 3S) enantiomer to form the optically active free base of such enantiomer.

SCHEME 1

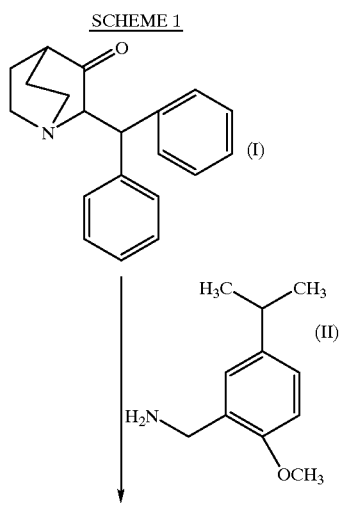

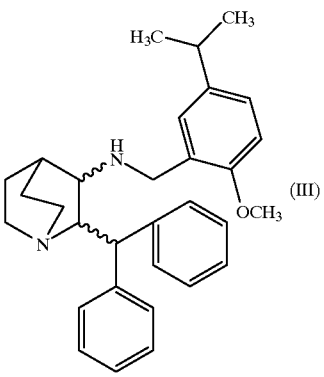

SCHEME 2

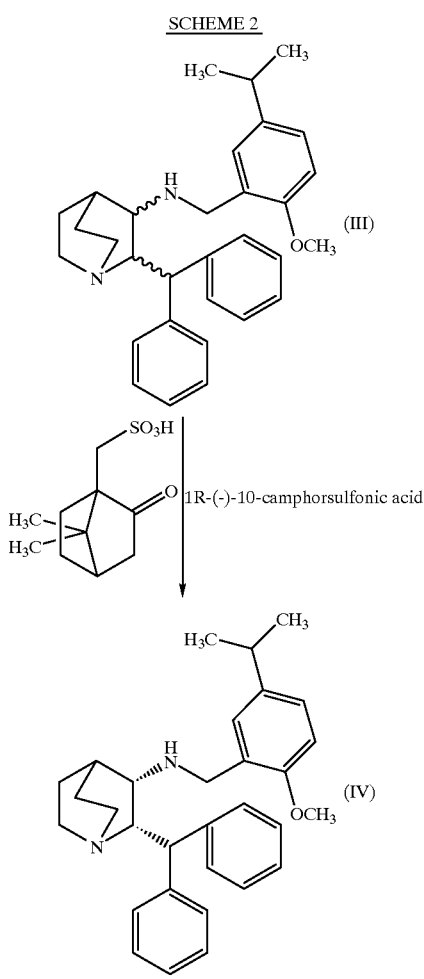

SCHEME 3

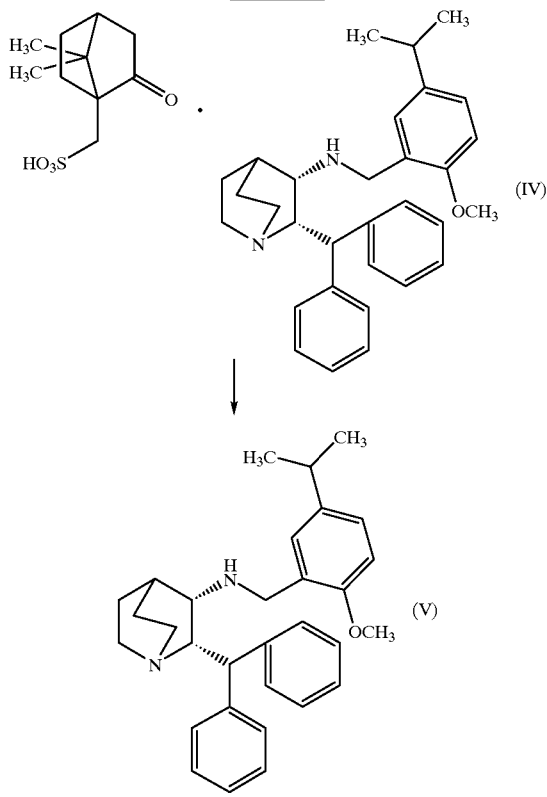

Referring to scheme 1, the racemate can be prepared by the following two step procedure. The first step is a reversible nucleophilic addition reaction of the compound of formula I with the compound of formula II in the presence of a catalytic amount of camphorsulfonic acid and a drying agent or apparatus designed to remove azeotropically the water generated (e.g., molecular sieves or a Dean Stark trap), to produce an imine intermediate of the formula

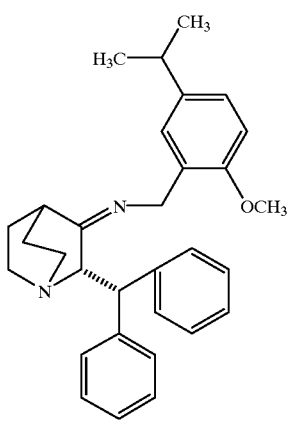

VIII

Suitable solvents for this reaction include toluene, dichloromethane, benzene and xylenes. Suitable drying agents/solvent systems include magnesium sulfate, titanium tetrachloride/dichloromethane, titanium isopropoxide/ dichloromethane and molecular sieves/THF. Magnesium sulfate is preferred. When a Dean-Stark trap is used, the solvent is preferably toluene. This reaction may be run at a temperature from about 25° C. to about 110° C. The reflux temperature of the solvent is preferred.

Examples of other catalysts that may be used in place of camphorsulfonic acid are methanesulfonic acid and para-toluenesulfonic acid.

The imine intermediate may be reacted in situ (as described in the Example) or after being isolated, with a reducing agent such as sodium triacetoxyborohydride, sodium cyanoborohydride, sodium borohydride, hydrogen and a metal catalyst, zinc and hydrochloric acid, borane dimethylsulfide or formic acid, to produce the racemate. Suitable reaction inert solvents for this reaction include non-ketone containing solvents such as lower alcohols (e.g., methanol, ethanol and isopropanol), acetic acid, chloroform, isopropyl ether, methylene chloride, tetrahydrofuran (THF), and combinations of the foregoing solvents, e.g., acetic acid in THF or acetic acid in methylene chloride. This reaction is generally carried out at a temperature from about 0° C. to about 30° C., preferably from about 0° C. to about 10° C. When sodium triacetoxyborohydride is the reducing agent, it is preferable that the solvent be other than a lower alcohol. Preferably, the reducing agent is sodium triacetoxyborohydride and the solvent is acetic acid in THF.

The resolution step, which is illustrated in scheme 2, comprises reacting 1-azabicyclo[2.2.2]octan-3-amine, 2-(diphenylmethyl)-N-[[2-methoxy-5-(1-methylethyl) phenyl]methyl] with 1R-(-)-10-camphorsulfonic acid in a solvent capable of dissolving both of the foregoing reagents and of selectively (i.e., preferentially) dissolving the camphorsulfonic acid salt of the corresponding (2R,3R) enantiomer relative to that of the (2S,3S) enantiomer, and stirring the mixture to form the optically active camphorsulfonic acid salt of (2S, 3S)-1-azabicyclo[2.2.2]octan-3-amine, 2-(diphenylmethyl)-N-[[2-methoxy-5-(1-methylethyl) phenyl]methyl]. The salt can then be isolated using conventional techniques (e.g., as described in section B, paragraph 1 of the Example, by stirring for several hours, filtering off the precipitate, washing the filter cake and vacuum drying).

The above resolution is preferably carried out under a nitrogen atmosphere. The reaction temperature can range from about 10° C. to about 50° C., with the higher temperatures in this range favoring optical purity over yield and the temperatures at the lower end of the range favoring yield over optical purity.

The camphorsulfonic acid salt of the (2S, 3S) enantiomer that is obtained from the above resolution process can be optionally repulped, as exemplified in section B, paragraph 2 of the Example, to increase the optical purity of the product.

The camphorsulfonic acid salt of (2S, 3S)-1-azabicyclo [2.2.2]octan-3-amine, 2-(diphenylmethyl)-N-[[2-methoxy-5-(1-methylethyl)phenyl] methyl] can also optionally be hydrolyzed, as depicted in scheme 3, to obtain the free base of the (2S, 3S) enantiomer. Such hydrolysis can be accomplished by reacting the salt with an appropriate alkaline agent using methods well known to those skilled in the art. For example, the optically active precipitate can be partitioned between dichloromethane and an aqueous base such as sodium or potassium hydroxide or potassium carbonate, or an alcoholic solution of the precipitate can be stirred with a basic ion exchange resin. The free base, which is obtained in solution, can then be isolated or converted in solution to the corresponding hydrochloric acid salt or other desired acid addition salt.

Another method by which the racemate can be prepared is described below. (This method can also be used to prepare the (2S, 3S) or (2R, 3R) enantiomer).

A compound of the formula

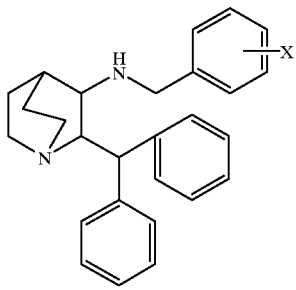

XI wherein X is hydrogen or methoxy, having the same absolute stereochemistry as the desired product, is subjected to hydrolytic removal of the benzyl or methoxybenzyl group to produce the corresponding compound of the formula

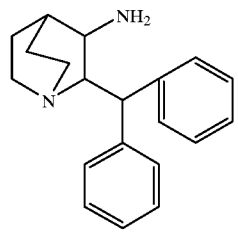

VI having the same desired stereochemistry, and then reacting the above compound so formed with an aldehyde of the formula

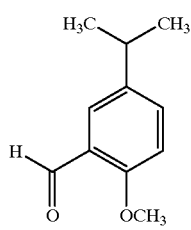

VII in the presence of a reducing agent.

Hydrolytic removal of the benzyl or methoxybenzyl group is generally carried out using a strong mineral acid such as hydrochloric, hydrobromic or hydroiodic acid, at a temperature from about room temperature to about the reflux temperature of the acid. Preferably, the reaction is conducted in hydrobromic acid at the reflux temperature. This reaction is usually carried out for a period of about 2 hours.

Alternatively, hydrolytic removal of the benzyl or methoxybenzyl group in the above procedure may be replaced by hydrogenolytic removal of such group. Hydrogenolytic removal is generally accomplished using hydrogen in the presence of a metal containing catalyst such as platinum or palladium. This reaction is usually conducted in a reaction inert solvent such as acetic acid or a lower alcohol, at a temperature from about 0° C. to about 50° C. The benzyl or methoxybenzyl group may also be removed, alternatively, by treating the compound of formula II with a dissolving metal such as lithium or sodium in ammonia at a temperature from about −30° C. to about 78° C., or with a formate salt in the presence of palladium or with cyclohexane in the presence of palladium.

Preferably, the benzyl or methoxybenzyl group is removed by treating the compound of formula XI with hydrogen in the presence of palladium hydroxide on carbon in methanol containing hydrochloric acid at a temperature of about 25° C.

The resulting compound of formula VI can be converted into the desired racemate (or enantiomer) by reaction with the aldehyde of formula VII in the presence of a reducing agent. The reaction is typically carried out using a reducing agent such as sodium cyanoborohydride, sodium triacetoxyborohydride, sodium borohydride, hydrogen and a metal catalyst, zinc and hydrochloric acid, borane dimethylsulfide or formic acid at a temperature from about −60° C. to about 50° C. Suitable reaction inert solvents for this reaction include non-ketone containing solvents such as lower alcohols (e.g., methanol, ethanol and isopropanol), acetic acid, methylene chloride, tetrahydrofuran (THF), and combinations of the foregoing solvents. Preferably, the solvent is methylene chloride, the temperature is about 25° C., and the reducing agent is sodium triacetoxyborohydrde.

Alternatively, the reaction of the compound of the formula VI with the compound of the formula VII may be carried out in the presence of a drying agent or using an apparatus designed to remove azeotropically the water generated, to produce an imine of the formula

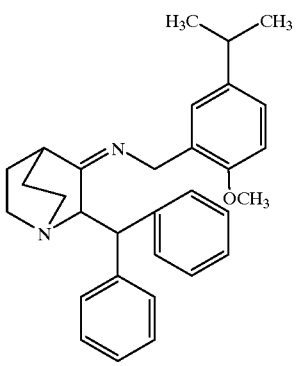

VIII which is then reacted with a reducing agent as described above, preferably with sodium triacetoxyborohydride at about room temperature. The preparation of the imine is generally carried out in a reaction inert solvent such as benzene, xylenes or toluene, preferably toluene, at a temperature from about 25° C. to about 110° C., preferably at about the reflux temperature of the solvent. Suitable drying agents/solvent systems include titanium tetrachloride/dichloromethane, titanium isopropoxide/dichloromethane and molecular sieves/THF. Titanium tetrachloride/dichloromethane is preferred.

The racemate (and both enantiomers) can also be prepared from a compound of the formula VI having the same stereochemistry by reacting the compound of formula VI with a compound of the formula

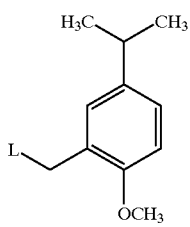

wherein L is a suitable leaving group (e.g., chloro, bromo, iodo or mesylate). This reaction is generally carried out in a reaction inert solvent such as dichloromethane or THF, preferably dichloromethane, at a temperature from about 0° C. to about 60° C., preferably at about 250° C.

The racemate (and both enantiomers) can also be prepared from a compound of the formula VI having the same stereochemistry by reacting the compound of formula VI with a compound of the formula

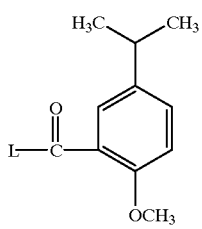

wherein L is defined as above or is imidazole, and then reducing the resulting amide. This reaction is typically carried out in an inert solvent such as THF or dichloromethane at a temperature from about −20° C. to about 60° C., preferably in dichloromethane at about −20° C. Reduction of the resulting amide is accomplished by treatment with a reducing agent such as borane dimethylsulfide complex, lithium aluminum hydride or diisobutylaluminum hydride in an inert solvent such as ethyl ether or THF. The reaction temperature may range from about 0° C. to about the reflux temperature of the solvent. Preferably, the reduction is accomplished using borane dimethylsulfide complex in THF at about 60° C.

The racemate and the (2S, 3S) enantiomer are basic in nature and are therefore capable of forming a wide variety of different salts with various inorganic and organic acids. Although such salts must be pharmaceutically acceptable for administration to animals, it is often desirable in practice to initially isolate the active compound from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the racemate and (2S, 3S) enantiomer can be readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The racemate and the (2S, 3S) enantiomer and their pharmaceutically acceptable salts (hereinafter also referred to as "the active compounds") exhibit substance P receptor binding activity and therefore are of value in the treatment and prevention of clinical conditions or disorders in mammals, including humans, the treatment or prevention of which can be effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, emesis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, sunburn, stroke, eye disorders, disorders related to immune enhancement or suppression such as systemic lupus erythematosus, disorders caused or mediated by angiogenesis or of which angiogenesis is a symptom, and rheumatic diseases such as fibrositis.

The active compounds can be administered via either the oral, parenteral or topical routes. In general, these compounds are most desirably administered in dosages ranging from about 0.5 mg to about 500 mg per day, although variations will necessarily occur depending upon the weight and condition of the subject being treated and the particular route of administration chosen. Variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The active compounds may be administered alone or in combination with pharmaceutically acceptable carriers or diluents by either of the three routes previously indicated, and such administration may be carried out in single or multiple doses. More particularly, such compounds can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compound or a pharmaceutically acceptable salt thereof is present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds topically when treating inflammatory conditions of the skin and this may preferably be done by way of creams, jellies, gels, pastes, ointments and the like, in accordance with standard pharmaceutical practice.

The activity of the active compounds as substance P receptor antagonists may be determined by its ability to inhibit the binding of substance P at its receptor sites in bovine caudate tissue, employing radioactive ligands to visualize the tachykinin receptors by means of autoradiography. The substance P antagonizing activity of such compounds may be evaluated by using the standard assay procedure described by M. A. Cascieri et al., as reported in the *Journal of Biological Chemistry*, Vol. 258, p. 5158 (1983). This method essentially involves determining the concentration of the active compound of this invention, or a pharmaceutically acceptable salt thereof, required to reduce by 50% the amount of radiolabelled substance P ligands at their receptor sites in said isolated cow tissues, thereby affording characteristic $IC_{50}$ values for the compound tested.

In this procedure, bovine caudate tissue is removed from a −70° C. freezer and homogenized in 50 volumes (w./v.) of an ice-cold 50 mM Tris (ie., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 40 g/ml of bacitracin, 4 μg/ml of leupeptin, 2 μg of chymostatin and 200 g/ml of bovine serum albumin. This step completes the production of the tissue preparation.

The radioligand binding procedure is then carried out in the following manner, viz., by initiating the reaction via the addition of 100 μl of the test compound made up to a concentration of 1 μM, followed by the addition of 100 μl of radioactive ligand made up to a final concentration 0.5 mM and then finally by the addition of 800 μl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The anti-psychotic activity of the active compounds as neuroleptic agents for the control of various psychotic disorders may be determined primarily by a study of its ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following Example. It will be understood, however, that the invention is not limited to the specific details of this example.

EXAMPLE

A. Racemic (±) (2R,3R; 2S,3S)-1-Azabicyclo[2.2.2]octan-3-amine, 2-(diphenylmethyl)-N-[[2-methoxy-5-(1methylethyl)phenyl]methyl]dihydrochloride dihydrate To a 125 cc 3-neck flask fitted with a mechanical stirrer, nitrogen inlet, Dean-Stark trap and reflux condenser was charged 10 gm of 2-diphenylmethyl-1-azabicyclo[2.2.2]octan-3-oxide (34.3 mmoles, 1 equiv.), 6.89 gm of 1-methoxy-2-aminomethyl-4-isopropylbenzene (38.43 mmoles 1.12 equiv.), 16 mg of 1R-(-)-10-camphorsulfonic acid (0.069 mmoles, 0.002 equiv.) and 45 cc of toluene. The resulting suspension was heated in an oil bath to reflux (110° C.). The reaction was heated at reflux for 3 hours and approx. 0.6 cc of water was seen to collect in the Dean-Stark trap. The reaction was allowed to cool to ambient temperature and stirred for 14 hours. The reaction mixture was transferred to a single neck flask and rotary evaporated to approx. 24 cc in volume. This concentrate was added dropwise to a 200 cc 3-neck flask fitted with mechanical stirrer, thermometer and nitrogen inlet and containing 18.18 gm (85.77 mmoles, 2.5 equiv.) of sodium triacetoxyborohydride and 10.3 gm (171.55 mmoles, 5 equiv.) of acetic acid in 60 cc of tetrahydrofuran pre-cooled in an ice/water bath to 0° C. The addition of the toluene concentrate was complete after 7 minutes and the internal temperature reached ±10° C. The ice bath was removed and the resulting heterogeneous reaction mixture was allowed to warm ambient temperature (24° C.) and stir for 14 hours. The reaction was followed by TLC (thin layer chromatography), using 100% ethyl acetate and ethyl acetate/methanol (2/1).

The reaction mixture was then rotary evaporated to approx. 40 cc in volume and then diluted with 150 cc of dichloromethane. This mixture was added to 200 cc of water with magnetic stirring and the total mixture was stirred for 15 minutes. The pH of this mixture was seen to be 4.0 and was adjusted to pH 11.0 by portionwise addition of a 25% sodium hydroxide solution. The organic and aqueous layers were then separated and the basic aqueous layer extracted (1×70 cc) with dichloromethane, after which the combined organic layers were dried over anhydrous magnesium sulfate for one hour. The drying agent was filtered off and the filtrate rotary evaporated to approximately 100 cc in volume. To this concentrate was added 160 cc of 2-propanol and the mixture was rotary evaporated again to approximately 100 cc in volume. The final concentrate was magnetically stirred at ambient temperature and, after 15 minutes, a white precipitate formed. This slurry was granulated for 2 hours. The white solids were filtered and the filtered cake was washed with 2-propanol and vacuum dried to give 7.68 gm (49% yield) of the title compound. Melting point=111–115° C.

An HPLC assay of the solids was run on a Hewlett Packard series 2 liquid chromatogram using a Zorbax CN column, 203 nm UV detector and a mobile phase of 55% acetonitrile/45% water (with 0.1% $H_3PO_4$+0.2% triethylamine (TEA)) with 1 ml/min flow rate. This analysis showed only the trans diastereomer present at 90% purity.

B. (2S-3S)-1-Azabicyclo[2.2.2]octan-3-amine, 2-(diphenylmethyl)-N-[[2-methoxy-5-(1-methylethyl)phenyl]methyl], (1R)-(-)-10-Camphorsulfonic acid salt To a 125 cc 3-neck flask fitted with a magnetic stirrer and nitrogen inlet was charged 5.11 gm of 1-azabicyclo[2.2.2]

octan-3-amine, 2-(diphenylmethyl)-N-[[2-methoxy-5-(1-methylethyl)phenyl]methyl] (11.24 mmoles, 1 equiv.) and 51 cc of acetonitrile to give a partial suspension. Then, 2.61 gm of (1R)-(-)-10-camphorsulfonic acid (11.24 mmoles, 1 equiv.) was added in one portion and the reaction became homogeneous. After stirring at ambient temperature for 5 minutes, a precipitate formed. Then, a further 5 cc of acetonitrile was added and the reaction was stirred for 4 hours. The solids were filtered off and the filter cake was washed (2×6 cc) with acetonitrile and vacuum dried to give a white solid having a weight of 2.97 gm (38.5% overall yield, 77% yield of desired enantiomeric salt). Melting point=177–182° C.

An HPLC assay of the crude salt (2.97 gm) was run on a Chrom Tech Chiral-AGP column. Mobile phase—0.01M $KH_2PO_4$ (pH=5.5): acetonitrile (85:15 v/v). Detection was 229 nm UV light, flow rate was 1 ml/min, injection volume was 20 uL. The assay showed 95.7% of the desired enantiomer and 4.3% of the undesired enantiomer.

Charged to a 35 cc flask fitted with magnetic stirrer were 2.87 gm of the above crude salt and 20 cc of acetonitrile, and the resulting slurry was stirred at ambient temperature for 5 hours. The solids were then filtered off and washed (2×3 cc) with acetonitrile and then vacuum dried to give a white solid. Weight=2.8 gm (97% mass recovery). Melting point= 180–185° C.

An HPLC assay of the repulped salt (2.8 gm) was run on a Chrom Tech Chiral-AGP column. Mobile phase—0.01 M $KH_2PO_4$ (pH=5.5): acetonitrile (85:15 v/v). Detection was 229 nm UV light, flow rate was 1 ml/min, injection volume was 20 uL. The assay showed 96.6% of the desired enantiomer and 3.4% of the undesired enantiomer.

The optical rotation of the repulped salt measured on a Perkin Elmer 241 polarimeter using a Sodium 589 light source. The repulped salt (44.9 mg) was dissolved in 10 cc of methanol and used to fill a 5 cc, 1 decimeter cell. $[\alpha]^{25}_D = -26.06°$.

C. (2S, 3S)-1-Azabicyclo[2.2.2]octan-3-amine,2-(diphenylmethyl)-N-[[2-methoxy-5-(1-methylethyl)phenyl]methyl]

In a 100 cc erlenmeyer flask fitted with magnetic stirrer was charged 2.63 gm (3.83 mmoles) of the repulped salt from step B above, 32 cc of dichloromethane and 16 cc of water to give a homogeneous biphasic solution. The pH of the aqueous layer was seen to be 4.0 and was adjusted to pH 11.00 with the dropwise addition of a 25% sodium hydroxide solution. After basification, the two layers were stirred for 15 minutes. The layers were separated, the organic layer was washed (1×16 cc) with water, the layers were separated, the organic layer was dried over anhydrous sodium sulfate for one hour, and the drying agent was filtered off. The organic layer was stripped to a foam/oil mixture that on standing at ambient temperature crystallized in two days. Weight=1.659 gm (95.3% yield). Melting point=100–103° C.

A chiral HPLC assay run on a Chrom Tech Chiral-AGP column (100 mm×4.0 mm, 5 μm). Mobile phase was 0.01 M $KH_2PO_4$ (pH=5.5): acetonitrile (85:15 v/v). Detection was 229 nm UV light, flow rate was 1 ml/min and injection volume was 20 uL The assay showed 99.5% of the desired enantiomer and 0.5% of the undesired enantiomer.

A purity HPLC assay run on a Zorbax Rx C-8 column (15 cm×4.6 mm I.D.). Mobile phase was acetonitrile: water: triethylamine: phosphoric acid (650:350:3:1, v/v). Detection was 229 nm UV light, flow rate was 2.0 ml/min and injection volume was 20 μL. The assay showed the product to be 99.5% pure.

The optical rotation of the optically active free base final product was measured on a Perkin Elmer 241 polarimeter using sodium 589 as a light source. The compound (52.4 mg) was dissolved in 10 cc of methanol and was used to fill a 5 cc cell 1 decimeter long. $[\alpha]^{25}_D = -9.27°$.

We claim:

1. A process for resolving racemic (±)-(2R,3R; 2S,3S)-1-azabicyclo-[2.2.2]octan-3-amine, 2-(diphenyl-methyl)-N-{[2-methoxy-5-(1-methyl-ethyl)-phenyl]methyl } of the formula:

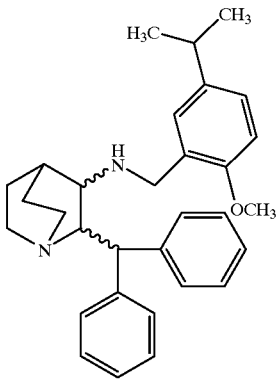

(III)

said process comprising:

1) reacting said racemate with 1R-(-)-10-camphorsulfonic acid of the formula:

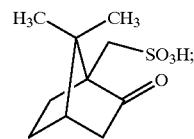

and 2) obtaining the 2S,3S enantiomer by substantially selectively precipitating and recovering the camphorsulfonic acid salt thereof of the structural formula:

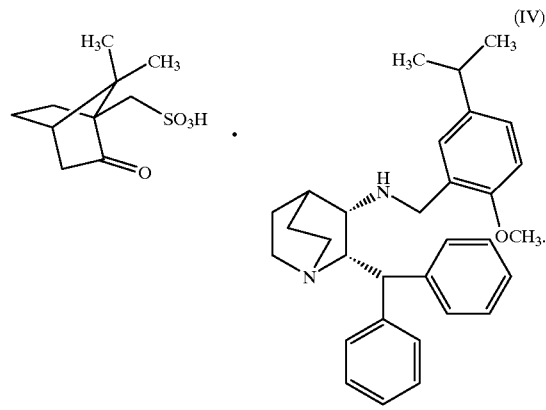

(IV)

2. A process according to claim 1, further comprising hydrolyzing said optically active salt that precipitates out of solution to obtain said (2S,3S) enantiomer as free base having the following structure:

(V)

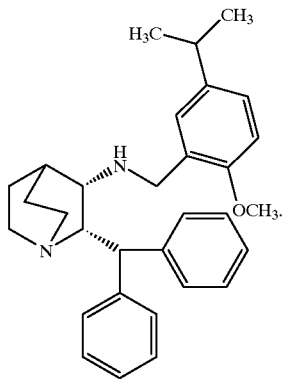

3. A process according to claim 1, wherein said resolving is conducted in a solvent and said solvent is acetonitrile.

4. A process according to claim 1, wherein said resolving is conducted in a solvent and said solvent is acetone.

5. A process according to claim 1, wherein said resolving is conducted in a solvent and said solvent is ethanol.

6. A process according to claim 3, further comprising hydrolyzing said optically active salt that precipitates out of solution to obtain said (2S,3S) enantiomer as free base having the following general structure:

(V)

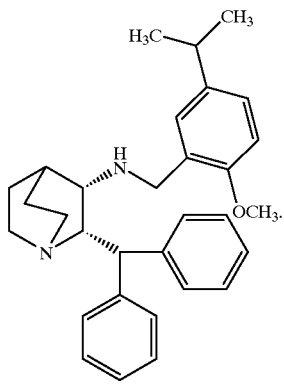

7. A process according to claim 1, wherein said substantially selectively precipitating and recovering of said camphorsulfonic acid salt is carried out in a solvent system capable of dissolving, the process reactants which comprise said process reactants comprising said racemate and said camphorsulfonic acid, and selectively dissolving substantially only the resulting optically active camphorsulfonic acid salt of said (2R,3R) enantiomer of said racemate, whereby isolation of said (2S,3S) enantiomer of said racemate is accomplished through precipitation and recovery thereof.

8. A process according to claim 2, wherein after said isolation by precipitation and recovery, said (2S,3S) enantiomer is further purified to at least 99.5% pure.

9. A process according to claim 8, wherein said (2S,3S) enantiomer is further purified to at least 99.99% pure.

10. A process for preparing (2S,3S) enantiomer of 1-azabicyclo-[2.2.2]octan-3-amine, 2-(diphenyl-methyl)-N-{[2-methoxy-5-(1-methyl-ethyl)phenyl]methyl} of the formula:

(V)

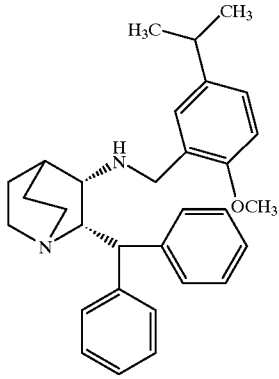

comprising:

1) reacting racemic (±)-(2S,2R)-1-azabicyclo-[2.2.2] octan-3-oxide, 2-diphenylmethyl of the formula:

(I)

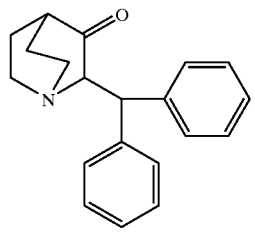

with 1-methoxy-2-aminomethyl-4-isopropylbenzene of the formula:

(II)

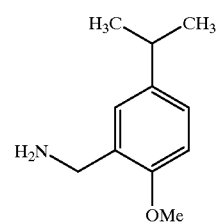

to yield racemic (±)-(2R,3R; 2S,3S)-1-azabicyclo-[2.2.2] octan-3-amine, 2-(diphenyl-methyl)-N-{[2-methoxy-5-(1-methyl-ethyl)phenyl]methyl } of the formula:

(III)

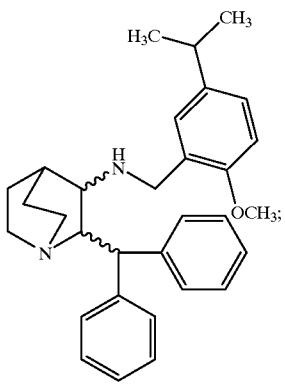

2) resolving said racemate produced in the preceding step by reacting it with 1R-(-)-10camphorsulfonic acid of the formula:

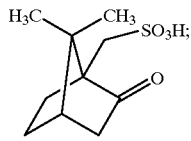

in a solvent system capable of dissolving said process reactants comprising said racemate and said camphorsulfonic acid, while selectively dissolving substantially only the resulting optically active camphorsulfonic acid salt of said (2R,3R) enantiomer of said racemate, whereby isolation of said (2S,3S) enantiomer of said racemate is accomplished through precipitation and recovery thereof as optically active camphorsulfonic acid salt of the formula:

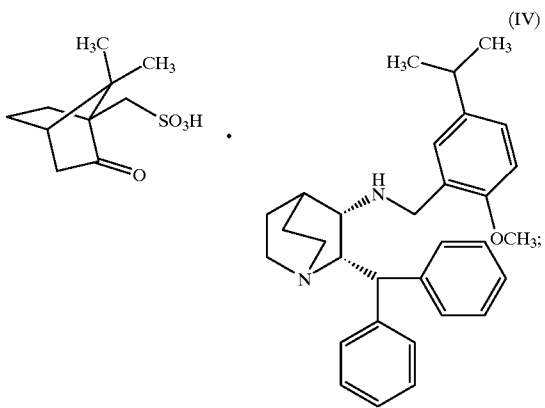

and 3) hydrolyzing said optically active salt that precipitates out of solution to obtain said (2S,3S) enantiomer as free base of the formula:

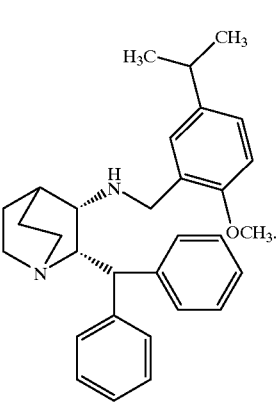

11. A process according to claim 10, wherein after said isolation by precipitation and recovery, and before said hydrolysis to free base, said (2S,3S) enantiomer is further purified to at least 99.5% pure.

12. A process according to claim 11, wherein said (2S,3S) enantiomer is further purified after said hydrolysis to said free base form thereof.

13. A process according to claim 10, wherein after said isolation by precipitation and recovery, and before said hydrolysis to free base, said (2S,3S) enantiomer is further purified to at least 99.99% pure.

14. A process according to claim 13 wherein said (2S,3S) enantiomer is further purified after said hydrolysis to said free base form thereof.

* * * * *